(12) United States Patent
Pazenok et al.

(10) Patent No.: US 9,145,369 B2
(45) Date of Patent: Sep. 29, 2015

(54) PROCESS FOR PREPARING 1-ALKYL-3-FLUOROALKYL-1H-PYRAZOLE-4-CARBOXYLIC ACID CHLORIDES

(71) Applicant: BAYER CROPSCIENCE AG, Monheim (DE)

(72) Inventors: Sergii Pazenok, Solingen (DE); Norbert Lui, Odenthal (DE); Thomas Norbert Mueller, Monheim (DE)

(73) Assignee: BAYER CROPSCIENCE AG, Monheim (DE)

( * ) Notice: Subject to any disclaimer, the term of this patent is extended or adjusted under 35 U.S.C. 154(b) by 0 days.

(21) Appl. No.: 14/400,359

(22) PCT Filed: May 10, 2013

(86) PCT No.: PCT/EP2013/059745
§ 371 (c)(1),
(2) Date: Nov. 11, 2014

(87) PCT Pub. No.: WO2013/171134
PCT Pub. Date: Nov. 21, 2013

(65) Prior Publication Data
US 2015/0126748 A1 May 7, 2015

(30) Foreign Application Priority Data

May 14, 2012 (EP) .................... 12167855

(51) Int. Cl.
*C07D 231/14* (2006.01)
(52) U.S. Cl.
CPC .................... *C07D 231/14* (2013.01)

(58) Field of Classification Search
None
See application file for complete search history.

(56) References Cited

U.S. PATENT DOCUMENTS

| | | | | |
|---|---|---|---|---|
| 5,223,526 | A * | 6/1993 | McLoughlin et al. | ........ 514/406 |
| 2010/0286221 | A1 | 11/2010 | Mansfield et al. | |
| 2013/0165664 | A1 | 6/2013 | Pazenok et al. | |

FOREIGN PATENT DOCUMENTS

| | | |
|---|---|---|
| EP | 2008996 A1 | 12/2008 |
| WO | 93/11117 A1 | 6/1993 |
| WO | 2004063165 A1 | 7/2004 |
| WO | 2006018725 A1 | 2/2006 |
| WO | 2007087906 A1 | 8/2007 |
| WO | 2008000834 A1 | 1/2008 |
| WO | 2008/086962 A2 | 7/2008 |
| WO | 2009003672 A2 | 1/2009 |
| WO | 2011061205 A1 | 5/2011 |
| WO | 2012010692 A1 | 1/2012 |

OTHER PUBLICATIONS

International Search Report from corresponding PCT/EP2013/059745, mailed Jun. 24, 2013.
Lee et al., "Synthesis and 13CNMR of (Trifluoromethyl) hydroxypyrazoles", J. Het. Chem., Feb. 1990, vol. 27, pp. 243-245.
Ahrens et al., "Preparation of benzoylhydrazines as agrochemical herbicides and insecticides", Database Chemabs, Columbus, Ohio; 2012, 3 pages, XP-002678085.

\* cited by examiner

*Primary Examiner* — Kamal Saeed
(74) *Attorney, Agent, or Firm* — Miles and Stockbridge

(57) ABSTRACT

The present invention relates to a novel method for preparing 1-alkyl-3-fluoroalkyl-1H-pyrazole-4-carbonyl chlorides, a useful precursor for the preparation of fungicides, by means of reductive dehalogenation, starting from N-alkyl-3-haloalkyl-5-halopyrazolecarbaldehyde.

12 Claims, No Drawings

PROCESS FOR PREPARING 1-ALKYL-3-FLUOROALKYL-1H-PYRAZOLE-4-CARBOXYLIC ACID CHLORIDES

CROSS REFERENCE TO RELATED APPLICATIONS

This application is a §371 National Stage Application of PCT/EP2013/059745, filed May 10, 2013, which claims priority to EP 12167855.1, filed May 14, 2012.

BACKGROUND

1. Field of the Invention

The present invention relates to a novel method for preparing 1-alkyl-3-fluoroalkyl-1H-pyrazole-4-carbonyl chlorides, a useful precursor for the preparation of fungicides, by means of reductive dehalogenation, starting from N-alkyl-3-haloalkyl-5-halopyrazolecarbaldehyde.

2. Description of Related Art

1-Alkyl-3-haloalkylpyrazolecarbonyl chlorides are important building blocks for preparing plant protection active ingredients, particularly SDHI fungicides. Unsubstituted pyrazolecarbonyl chlorides are typically prepared by reacting carboxylic acids with a chlorinating agent. One advantage of this method is that the corresponding carboxylic acids are readily accessible and are thus available on an industrial scale. This prerequisite is not satisfied for the preparation of substituted pyrazolecarbonyl chlorides, since the corresponding carboxylic acids are not readily accessible. 1-Alkyl-3-haloalkylpyrazolecarbonyl chlorides are typically prepared in a multi-stage transformation starting from fluoroalkylacetoacetate:

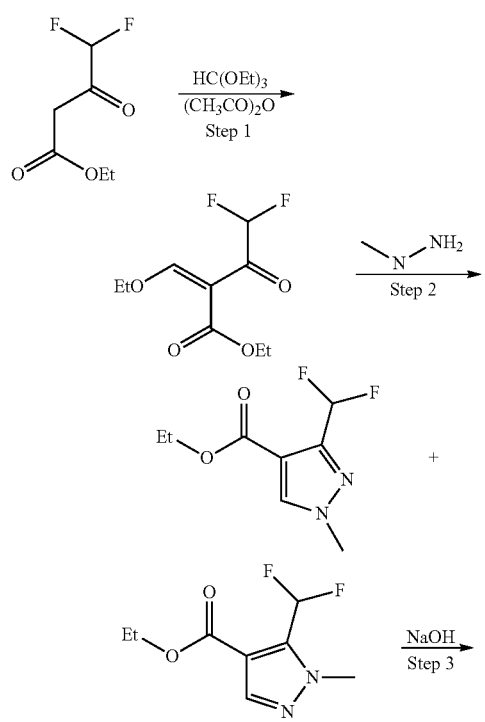

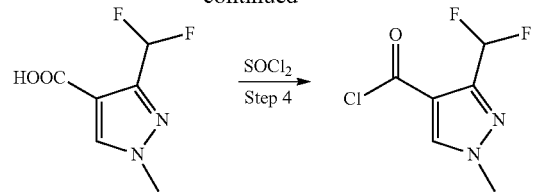

Steps 1 and 2 are particularly technically demanding. In step 1 a very large excess (2 to 3 equivalents) of acetic anhydride is required in order to ensure a complete transformation. The isolation of the product from step 1 and separation thereof from the excess acetic anhydride or acetic acid is costly and very time-consuming. In step 2, the formation of the second isomer (up to 15%) and the separation thereof renders the method difficult and costly.

SUMMARY

It has now been found that 1-alkyl-3-fluoroalkyl-1H-pyrazole-4-carbonyl chlorides of the formula (I)

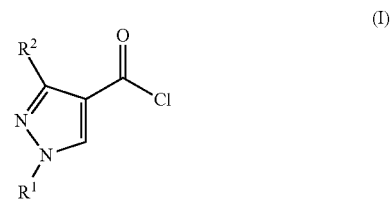

(I)

where $R^1$ is $C_1$-$C_6$-alkyl and $R^2$ is $C_1$-$C_5$-fluoroalkyl, are obtained by reacting 5-halo-1-alkyl-3-fluoroalkyl-1H-pyrazole-4-carbaldehyde of the formula (II)

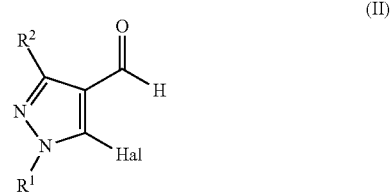

(II)

where Hal is Cl, Br or I and
$R^1$ and $R^2$ have the meanings stated above,
in a first step by means of catalytic hydrogenation and in the presence of a base to give 1-alkyl-3-fluoroalkyl-1H-pyrazole-4-carbaldehyde of the formula (III)

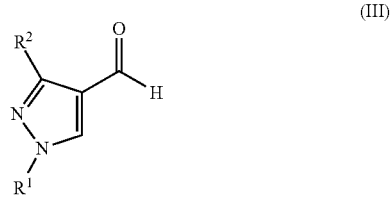

(III)

where $R^1$ and $R^2$ have the meanings stated above, and then the compounds of the formula (III) are converted into the acyl chlorides of the formula (I) by reaction with a chlorinating agent with addition of a free-radical initiator (step 2).

DETAILED DESCRIPTION OF A PREFERRED EMBODIMENT

The method according to the invention may be illustrated by the following formula scheme:

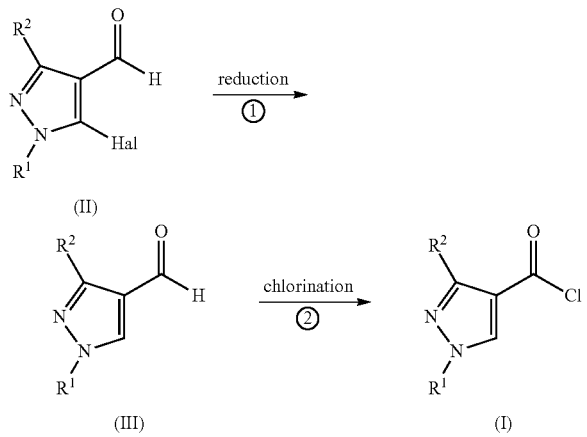

The 5-halo-1-alkyl-3-fluoroalkyl-1H-pyrazole-4-carbaldehydes used as starting materials in carrying out the method according to the invention are generally defined by the formula (II). The radical $R^1$ in this formula (II) is preferably methyl, ethyl, n-propyl, isopropyl, butyl, pentyl particularly preferably methyl. The radical $R^2$ is $C_1$-$C_5$-fluoroalkyl, where fluoroalkyl is an alkyl group having 1 to 5 carbon atoms which has been substituted with at least one fluorine atom up to the point of perfluorination. If the fluoroalkyl is not perfluorinated, further halogen atoms, such as chlorine and bromine, preferably chlorine, may be present as further substituents. $R^2$ is preferably $CF_2H$, $CF_3$, $CF_2Cl$, $CCl_2F$, $C_2F_5$, $C_3F_7$ particularly preferably $CF_2H$ and $CF_3$. 5-Chloro-1-methyl-3-difluoromethyl-1H-pyrazole-4-carbaldehyde (II-1) is very particularly preferably used as starting material.

Hal is Cl, Br or I, preferably Cl or Br, particularly preferably Cl.

WO 93/011117 A1 discloses the synthesis of a 1-methyl-3-trifluoromethyl-4-pyrazolecarboxylic acid, starting from the corresponding carboxaldehyde. WO 93/011117 A1, however, does not disclose the inventive synthesis of a pyrazolecarbonyl chloride from the corresponding carboxaldehyde. The inventive dehalogenation step by means of catalytic hydrogenation is also not disclosed in WO 93/011117 A1.

WO 2008/086962 A2 discloses a method for preparing substituted pyrazolecarbonyl chlorides halogenated in the 5-position from the corresponding aldehyde. The inventive dehalogenation step by means of catalytic hydrogenation is also not disclosed in WO 2008/086962 A2.

WO 2004/063165 A1 describes the removal of a chlorine atom in N-aryl-3-methyl-5-chloropyrazole-carbaldehydes. The reduction of 5-halo-N-alkyl-3-haloalkylpyrazole-4-carbaldehydes is not known in the prior art. At the same time, it is known that a haloalkyl group ($CF_2Cl$) in position 3 of 1-substituted-pyrazole-4-carboxylate can be partially reduced, forming 1-substituted 3-halo-3-fluoroalkylpyrazole-4-carboxylic acids (WO 2012/010692 A1).

It has now surprisingly been found that, under specific conditions, it is possible to selectively remove a halogen atom from N-alkyl-3-haloalkyl-5-halopyrazolecarbaldehyde, without affecting or reducing the haloalkyl group in position 3 and also without reducing the aldehyde group in position 4.

5-Halo-1-alkyl-3-fluoroalkyl-1H-pyrazole-4-carbaldehydes of the formula (II) are known or can be prepared by known methods (cf. *J. Het. Chem.* 1990, 27, 243, WO 2006/018725 A1, WO 2011/061205 A1).

5-Halo-1-alkyl-3-fluoroalkyl-1H-pyrazole-4-carbaldehydes of the formula (II) can be prepared in a simple and convenient manner, for example, (a) by reacting esters of the formula (V)

where $R^2$ has the meanings stated above and $R^3$ is methyl or ethyl,
with ethyl acetate in the presence of a base (e.g. sodium hydride or Na ethoxide) to give β-ketoesters of the formula (VI)

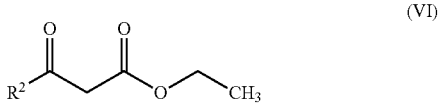

where $R^2$ has the meanings stated above, and this
(b) is reacted with alkylhydrazines of the formula (VII)

where $R^1$ has the meanings stated above,
in the presence of a diluent (e.g. toluene) to give 5-hydroxypyrazoles of the formula (VIII)

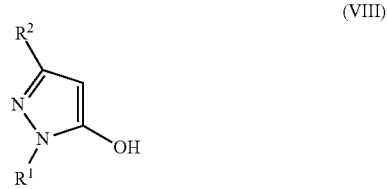

where $R^1$ and $R^2$ have the meanings stated above, and this
(c) is reacted in a final step with a halogenating agent (e.g. phosphoryl chloride, phosphoryl bromide or phosphoryl iodide), optionally in the presence of a diluent (e.g. toluene), or without a diluent, and in the presence of dimethylformamide.

Each step of this method is carried out using convenient starting materials and is completely regioselective.

Step 1: Reduction/catalytic Hydrogenation

Reductive dehalogenation by means of catalytic hydrogenation is not known for 5-halo-1-alkyl-3-fluoroalkyl-1H- pyrazole-4-carbaldehydes. In this regard, it might be expected that, under the reaction conditions, the aldehyde group will also at least partially react. Surprisingly, the pyrazole derivatives of the formula (II) react selectively under the reaction conditions to give pyrazole derivatives of the formula (III).

It is also regarded as surprising that the reductive dehalogenation of 5-halo-1-alkyl-3-fluoroalkyl-1H-pyrazole-4-carbaldehydes leads selectively and in high yield to the 1-alkyl-3-fluoroalkyl-1H-pyrazole-4-carbaldehydes.

The reaction temperatures may be varied in a relatively wide range when carrying out the method according to the invention. Generally, temperatures of 0° C. to 180° C., preferably temperatures of 0° C. to 100° C. and particularly preferably temperatures of 20° C. to 80° C., are employed.

The reaction time may be up to 20 hours, depending on the reactivity of the reactants, while the reaction can also be terminated earlier when conversion is complete. Preference is given to reaction times of 3-10 hours.

The reaction is carried out in the presence of hydrogen. It is possible to use either pure hydrogen or mixtures of hydrogen and an inert gas (up to 1:1), such as nitrogen or argon. The reaction is carried out at pressures of 1 bar to 50 bar, preferably 1 bar to 20 bar and particularly preferably 2 bar to 10 bar.

To scavenge the hydrogen chloride, hydrogen bromide or hydrogen iodide formed during the reaction, a base is added. As added base, either an inorganic base such as sodium carbonate, potassium carbonate, sodium bicarbonate, potassium bicarbonate, mono-, di- or trisodium phosphate or tripotassium phosphate, sodium hydroxide or potassium hydroxide or an organic base such as triethylamine, tributylamine, diazabicycloundecene (DBU), diazabicyclononene (DBN), pyridine, lutidine, 2-, 3- or 4-picoline or diazabicyclooctane (DABCO) can be used. Preference is given to the use of triethylamine. 0.5 to 20 molar equivalents, preferably 0.5 to 5 molar equivalents and particularly preferably 1 to 5 molar equivalents of the base are added, based on the substrate.

For the catalytic hydrogenation for reducing the compound of the general formula (II), any hydrogenation catalyst may be used as catalyst. Suitable catalysts include optionally one or more metals from groups 8-10 of the periodic table on any conventional inorganic support. Examples include noble metal catalysts, such as ruthenium catalysts, palladium catalysts, platinum catalysts and rhodium catalysts, Raney nickel catalysts and Raney cobalt and Lindlar catalysts. In addition to these heterogeneous catalysts, hydrogenations over homogeneous catalysts can, however, also be carried out, for example over the Wilkinson catalyst. The relevant catalysts may be used in supported form, for example on carbon (charcoal or activated charcoal), aluminium oxide, silicon dioxide, zirconium dioxide, calcium carbonate or titanium dioxide. Catalysts of this kind are known per se to those skilled in the art. Particularly preferred are palladium catalysts supported on calcium carbonate. The catalysts may be used either in water-moist or in dried form. The catalyst used is preferably reused for a plurality of conversions. In the method according to the invention, the catalyst is used at a concentration of approximately 0.01 to approximately 30% by weight, based on the halo-1-alkyl-3-fluoroalkyl-1H-pyrazole-4-carbaldehyde of the formula (II) used. The catalyst is preferably used at a concentration of approximately 0.1 to approximately 5% by weight.

The reaction is carried out in the presence of a solvent. Suitable solvents are: alcohols, ethyl acetate, isopropyl acetate, THF, methyltetrahydrofuran, dioxane, toluene, hexane, heptane, pentane or petroleum ether. Particular preference is given to the use of methanol, ethanol, DMSO, dimethylacetamide, DMF or NMP.

Step 2: Chlorination

The radicals $R^1$ and $R^2$ in formula (III) have the meanings stated above. Very particular preference is given to 1-methyl-3-difluoromethyl-1H-pyrazole-4-carbaldehyde (III-1) and 1-methyl-3-trifluoromethyl-1H-pyrazole-4-carbaldehyde (III-2), particularly the compound (III-1).

The chlorination of pyrazole aldehydes to acyl chlorides has been described in WO 2008/086962.

Typically, the 1-alkyl-3-fluoroalkyl-1H-pyrazole-4-carbaldehyde of the formula (III) and the chlorinating agent are used in a molar ratio of 1:3 to 1:2, preferably 1:1.4 to 1:1.

Chlorine or a chlorine-releasing agent can be used as chlorinating agent. The reaction can optionally be carried out in the presence of an inert diluent gas, such as nitrogen, carbon dioxide or noble gases. Suitable chlorinating agents, without making any claim to completeness, are for example $Cl_2$, $SO_2Cl_2$, $SOCl_2$, N-chlorosuccinimide or a mixture thereof. Preference is given to using $Cl_2$, $SO_2Cl_2$, or a mixture thereof as chlorinating agent. Particular preference is given to the use of $SO_2Cl_2$ and $Cl_2$ as chlorinating agents.

The reaction of 1-alkyl-3-fluoroalkyl-1H-pyrazole-4-carbaldehydes of the formula (III) with the chlorinating agent is carried out typically in the presence of a diluent which is inert under the prevailing reaction conditions. The diluent used can be, for example, mono-chlorinated or poly-chlorinated aliphatic or aromatic hydrocarbons or mixtures thereof. Examples of suitable diluents are chlorobenzene, dichlorobenzenes, trichlorobenzenes, chlorotoluenes, chlorobenzotrifluorides, methylene chloride, dichloroethane, chloroform, carbon tetrachloride. Preferred diluents are chlorobenzene, 1,2-dichlorobenzene, 1,3-dichlorobenzene, 1,4-dichlorobenzene, 1,2,3-trichlorobenzene, 1,2,4-trichlorobenzene, 4-chlorotrifluoromethylbenzene, 1,3,5-trichlorobenzene, 2-chlorotoluene, 3-chlorotoluene, 4-chlorotoluene or a mixture thereof. Particular preference is given to the use of chlorobenzene and dichlorobenzene.

The diluent is typically used in a ratio of 20:1 to 1:20, preferably 10:1 to 1:10, based on the substituted aldehyde (III).

According to the present invention, the chlorination is carried out under free-radical conditions. The prerequisite for this is the formation of chlorine free radicals.

It is known that organic peroxides or azo compounds decompose to free radicals under the action of heat and/or light, which initiate the free-radical chlorination.

Examples, without any claim of completeness, of suitable peroxides and azo compounds are tert-butyl hydroperoxide, dibenzoyl peroxide, di(4-tert-butylcyclohexyl) peroxydicarbonate, 2,2'-azobis(isobutyronitrile), dimethyl 2,2'-azobis (isobutyrate), 2,2'-azobis(2,4-dimethylvaleronitrile), di(2-ethylhexyl) peroxydicarbonate, tert-butyl peroxypivalate, tert-amyl peroxy-2-ethylhexanoate, tert-butyl peroxy-2-ethylhexanoate.

Preference is given to using the following free-radical initiators: 2,2'-azobis(isobutyronitrile), 2,2'-azobis(2,4-dimethylvaleronitrile), di(2-ethylhexyl) peroxydicarbonate, tert-amyl peroxy-2-ethylhexanoate, tert-butyl peroxy-2-ethylhexanoate. The free-radical initiator is typically used in an amount of 0.01 to 1 mol %, preferably 0.1 to 0.5 mol %, based on the aldehyde of the formula (III).

All methods according to the invention are generally carried out at standard pressure. It is, however, also possible to operate under elevated or reduced pressure—generally between 0.1 bar and 10 bar.

In place of the chlorination, the 1-alkyl-3-fluoroalkyl-1H-pyrazole-4-carbaldehydes of the formula (III) can alternatively be converted by reaction with a perhaloacid (e.g. periodic acid) in the presence of a diluent (e.g. acetonitrile) and in the presence of an oxidising agent (e.g. pyridinium chlorochromate (PCC)), to give the 1-alkyl-3-fluoroalkyl-1H-pyrazole-4-carboxylic acid of the formula (IV)

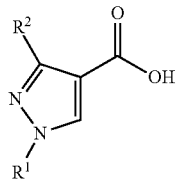

(IV)

where R¹ and R² have the meanings stated above.

Both the 1-alkyl-3-fluoroalkyl-1H-pyrazole-4-carbaldehydes of the formula (III) and the 1-alkyl-3-fluoroalkyl-1H-pyrazole-4-carboxylic acids of the formula (IV) are important intermediates in the synthesis of plant protection agents (cf. e.g. WO 2007/087906).

The preparation of 1,3-dialkyl-1H-pyrazole-4-carbonyl chlorides of the formula (I) in accordance with the invention is described in the following examples, which further illustrate the description above. The examples, however, shall be interpreted in a non-limiting manner.

PREPARATION EXAMPLES

Example 1

1-Methyl-3-difluoromethyl-1H-pyrazole-4-carbaldehyde (III-1)

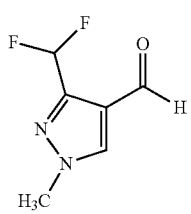

(III-1)

In an autoclave, 10 g of 5-chloro-3-(difluoromethyl)-1-methyl-1H-pyrazole-4-carbaldehyde were dissolved in 150 ml of ethanol, and 10.4 g of triethylamine and 500 mg of 5% palladium on calcium carbonate were added. The autoclave was flushed with nitrogen and subsequently pressurised to 5 bar hydrogen. The reaction mixture was then stirred at 30° C. for 4 h. After filtration of the catalyst, the solvent was removed under reduced pressure and the product was obtained as a solid (7.4 g) having a melting point of 46-47° C.

¹H NMR (CDCl₃) 4.1 (s, 3H), 6.85 (t, 1H), 7.73 (s, 1H), 10.1 (s, 1H) ppm.

Example 2

Ethyl 4,4-difluoro-3-oxobutanoate (VI-1)

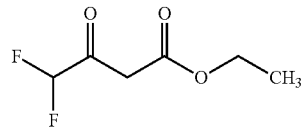

(VI-1)

Under a nitrogen atmosphere, 46.7 g (1.168 mol) of sodium hydride (60% dispersion in paraffin) were added to 600 ml of tetrahydrofuran. A mixture of 125 g (1.008 mol) of difluoroethyl acetate and 88.7 g (1.010 mol) of ethyl acetate was added dropwise at 35° C., while the temperature was kept below 40° C. The mixture was then further stirred at room temperature overnight. The reaction mixture was carefully poured into 1.7 l of ice water and the pH adjusted to pH 3 by addition of sulphuric acid. The mixture was extracted twice, each time with 500 ml of methyl tert-butyl ether, and the combined organic phases were washed twice with saturated sodium chloride solution, dried over sodium sulphate, concentrated at 40° C. and 150 mbar and distilled at 60 mbar (Vigreux column). The product was obtained at 85-87° C. as a colourless liquid (104 g, 62% of theory with a purity of >99% (GC)).

Example 3

3-(Difluoromethyl)-1-methyl-1H-pyrazol-5-ol (VIII-1)

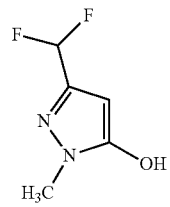

(VIII-1)

166 g (1 mol) of ethyl 4,4-difluoro-3-oxobutanoate were charged in 500 ml of methyl tert-butyl ether and treated with 140 g of formic acid. After cooling of the mixture to 5° C., 119 g (as 40% aqueous solution) of monomethylhydrazine were added. The mixture was then stirred for 20 h at 22° C. The phases were separated, and the organic phase was washed with 200 ml of water and dried over MgSO₄. After the removal of the solvent under reduced pressure, 148 g of the product was obtained as an yellow solid having an m.p. of 133° C. and a purity of 95%. Yield 95%.

Example 4

5-Chloro-3-(difluoromethyl)-1-methyl-1H-pyrazole-4-carbaldehyde (II-1)

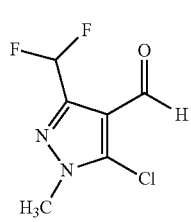

(II-1)

To a solution of 137.5 g (929 mmol) of 3-(difluoromethyl)-1-methyl-1H-pyrazol-5-ol in 136 ml (1858 mmol) of dimethylformamide and 750 ml of toluene was added dropwise with cooling 571 g (3716 mmol) of phosphoryl chloride. The mixture was heated for 3 hours under reflux and allowed to cool, and the reaction mixture wash carefully poured into 4 l of ice water. The product was extracted three times, each time with 1500 ml of ethyl acetate, and the combined organic phases were washed twice with saturated sodium bicarbonate solution and finally with saturated sodium chloride solution, dried over sodium sulphate and concentrated. 138 g (with a purity of >99% (GC)) of 5-chloro-3-(difluoromethyl)-1-methyl-1H-pyrazole-4-carbaldehyde (II-1) in the form of a yellow-brown solid was obtained, which was used without further purification in the next reaction step.

Example 5

1-Methyl-3-difluoromethyl-1H-pyrazole-4-carbonyl chloride

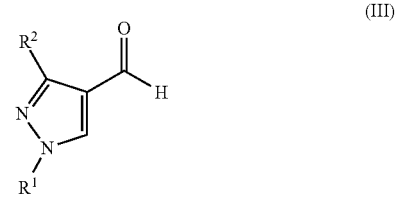

The solution of 16 g (100 mol) of 1-methyl-3-difluoromethyl-1H-pyrazole-4-carbaldehyde, 13.5 g (100 mmol) of sulphuryl chloride and 0.2 g of 2,2-azoisobutyronitrile in 50 ml of chlorobenzene was stirred at 70-80° C. for 6 h. The reaction solution was concentrated. 18.8 g of the product (95% yield) was obtained as an oil with a purity (GC) of 98%.

The invention claimed is:

1. Method for preparing 1-alkyl-3-fluoroalkyl-1H-pyrazole-4-carbonyl chloride of formula (I)

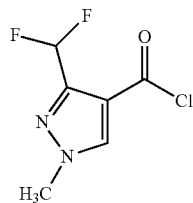

where $R^1$ is $C_1$-$C_6$-alkyl and $R^2$ is $C_1$-$C_5$-fluoroalkyl, comprising reacting a 5-halo-1-alkyl-3-fluoroalkyl-1H-pyrazole-4-carbaldehyde of formula (II)

where $R^1$ and $R^2$ have the meanings stated above and Hal is Cl, Br or I, by catalytic hydrogenation and with addition of a base to give 1-alkyl-3-fluoroalkyl-1H-pyrazole-4-carbaldehyde of formula (III)

where $R^1$ and $R^2$ have the meanings stated above, and then the compound of formula (III) is converted into the acyl chloride of formula (I) by reaction with a chlorinating agent with addition of a free-radical initiator.

2. Method according to claim 1, wherein 5-halo-1-alkyl-3-fluoroalkyl-1H-pyrazole-4-carbaldehyde of formula (II) where $R^1$ is methyl, ethyl, n-propyl, isopropyl, butyl, pentyl, $R^2$ is $CF_2H$, $CF_3$, $CF_2Cl$, $CCl_2F$, $C_2F_5$, $C_3F_7$ and Hal is Cl is used.

3. Method according to claim 1, wherein 5-halo-1-alkyl-3-fluoroalkyl-1H-pyrazole-4-carbaldehyde of formula (II) where $R^1$ is methyl, $R^2$ is $CF_2H$ or $CF_3$ and Hal is Cl is used.

4. Method according to claim 1, wherein 5-chloro-1-methyl-3-difluoromethyl-1H-pyrazole-4-carbaldehyde (II-1) is used.

5. Method according to claim 1, wherein the catalytic hydrogenation is carried out using a palladium catalyst supported on calcium carbonate.

6. Method according to claim 1, wherein catalytic hydrogenation is carried out at a temperature of 0° C. to 100° C.

7. Method according to claim 1, wherein catalytic hydrogenation is carried out at a pressure of 1 to 20 bar.

8. Method according to claim 1, wherein the base added to the catalytic hydrogenation is triethylamine.

9. Method according to claim 1, wherein 0.5 to 5 molar equivalents of base, based on the compound of formula (II), is added in the catalytic hydrogenation.

10. Method according to claim 1, wherein $SO_2Cl_2$ is used as chlorinating agent.

11. Method according to claim 1, wherein the free-radical initiator is selected from the group consisting of 2,2'-azobis(isobutyronitrile), 2,2'-azobis(2,4-dimethylvaleronitrile), di(2-ethylhexyl) peroxydicarbonate, tert-amyl peroxy-2-ethylhexanoate and tert-butyl peroxy-2-ethylhexanoate.

12. Method according to claim 1, wherein the free-radical initiator is used in an amount from 0.1 to 0.5 mol %, based on the 1-alkyl-3-fluoroalkyl-1H-pyrazole-4-carbaldehyde of formula (III).

* * * * *